US009376435B2

(12) United States Patent
George et al.

(10) Patent No.: US 9,376,435 B2
(45) Date of Patent: Jun. 28, 2016

(54) CHROMOPHORES FOR THE DETECTION OF VOLATILE ORGANIC COMPOUNDS

(75) Inventors: Subi Jacob George, Bangalore (IN); Mohit Kumar, Bihar (IN)

(73) Assignee: Jawaharlal Nehru Centre For Advanced Scientific Research, Jakkur, Bangalore (IN)

( * ) Notice: Subject to any disclaimer, the term of this patent is extended or adjusted under 35 U.S.C. 154(b) by 389 days.

(21) Appl. No.: 13/489,876

(22) Filed: Jun. 6, 2012

(65) Prior Publication Data

US 2013/0078731 A1    Mar. 28, 2013

(30) Foreign Application Priority Data

Sep. 23, 2011    (IN) .......................... 3299/CHE/2011

(51) Int. Cl.
*G01N 21/64*    (2006.01)
*C07D 471/06*    (2006.01)

(52) U.S. Cl.
CPC .......... *C07D 471/06* (2013.01); *G01N 21/6428* (2013.01); *G01N 2021/6439* (2013.01)

(58) Field of Classification Search
None
See application file for complete search history.

(56) References Cited

U.S. PATENT DOCUMENTS

2007/0221913 A1*    9/2007    Lee et al. ..................... 257/40

FOREIGN PATENT DOCUMENTS

WO    WO 2009/118742    * 10/2009    ........... C07D 471/06

OTHER PUBLICATIONS

See, K. C. et al, Enhanced Response of n-Channel Naphthalenetetracarboxylic Diimide Transistors to Dimethyl Methylphosphonate Using Phenolic Receptors, 2007, Advanced Materials, vol. 19, pp. 3322-3327.*
Juskowiak, B. et al. Enhanced fluorescence of the Eu3+-naphthalenediimide derivative-phenanthroline ternary complex and the determination of DNA, 2004, Analytics Chimica Acta, vol. 512, pp. 133-139.*
Lin, C. et al. Synthesis and characterization of naphthalene diimide (NDI)-based near infrared chromophores with two-photon absorbing properties, 2010, Tetrahedron, vol. 66, pp. 8629-8634.*
An et al., Color-Tuned Highly Fluorescent Organic Nanowires/Nanofabrics: Easy Massive Fabrication and Molecular Structural Orgin, *J Am Chem Soc* (Mar. 25, 2009), 131(11):3950-3957.
Ajayaghosh et al., Hydrogen-Bonded Assemblies of Dyes and Extended π-Conjugated Systems, *Topics in Current Chemistry* (Aug. 15, 2005), 258:83-118 (Abstract).
Babu et al., Excited State Processes in Linear π-System-Based Organogels, *J Phys Chem Lett* (Nov. 18, 2010), 1(23):3413-3424 (Abstract).
Carturan et al., Optical properties of free-base tetraphenylporphyrin embedded in fluorinated polyimides and their ethanol and water vapours sensing capabilities, *Sensors and Actuators B: Chemical* (Mar. 28, 2009), 137(1):281-290 (Abstract).
Che et al., Expedient vapor probing of organic amines using fluorescent nanofibers fabricated from an n-type organic semiconductor, *Nano Lett* (Aug. 2008), 8(8):2219-2223 (Abstract).

(Continued)

*Primary Examiner* — Robert Xu
(74) *Attorney, Agent, or Firm* — Pepper Hamilton LLP (57) ABSTRACT

Aromatic diimide chromophores and methods for using the chromophores for the detection of volatile organic compounds are described. The chromophores are able to reversibly change colors in the presence or absence of volatile organic compounds.

9 Claims, 4 Drawing Sheets

BLUE FLUORESCENCE

GREEN FLUORESCENCE

(56) References Cited

OTHER PUBLICATIONS

Chen et al., Self-assembled n-stacks of functional dyes in solution: structural and thermodynamic features, *Chem Soc Rev* (Sep. 2, 2008), 38:564-584 (Abstract).

Dickinson et al., A chemical-detecting system based on a cross-reactive optical sensor array, *Nature* (Aug. 22, 1996), 382(6593):697-700 (Abstract).

Dong et al., Aggregation-induced emissions of tetraphenylethene derivatives and their utilities as chemical vapor sensors and in organic light-emitting diodes, *Applied Physics Letters* (May 16, 2007), 91:011111:1-3.

Effenberger et al., 5-Dimethylamino-5'-nitro-2,2'-bithiophene-a New Dye with Pronounced Positive Solvatochromism, *Angew Chem Int Ed Engl* (1993), 32(5):719-721.

Esser et al., Detection of ethylene gas by fluorescence turn-on of a conjugated polymer, *Angew Chem Int Ed Engl* (Nov. 15, 2010), 49(47):8872-8875 (Abstract).

Gao et al., Electrosynthesis of oligo(methoxyl pyrene) for turn-on fluorescence detection of volatile aromatic compounds, *J Mater Chem* (Nov. 27, 2009), 20:2993-2998 (Abstract).

Giansante et al., Time-resolved confocal fluorescence microscopy of trinitrobenzene-responsive organic nanofibers, *Anal Bioanal Chem* (Jan. 2010), 396(1):125-131 (Abstract).

Hoeben et al., About Supramolecular Assemblies of π-Conjugated Systems, *Chem Rev* (Jun. 24, 2004), 105:1491-1546.

Jayanty et al., Enhanced fluorescence of remote functionalized diaminodicyanoquinodimethanes in the solid state and fluorescence switching in a doped polymer by solvent vapors, *Chemistry* (Feb. 6, 2004), 10(3):791-797 (Abstract).

Jonkheum et al., Probing the Solvent-Assisted Nucleation Pathway in Chemical Self-Assembly, *Science* (Jul. 7, 2006), 313(5783):80-83 (Abstract).

Kumar et al., Spectroscopic probing of the dynamic self-assembly of an amphiphilic naphthalene diimide exhibiting reversible vapochromism, *Chemistry* (Sep. 26, 2011), 17(40):11102-11106 (Abstract).

Kumar et al., Solid State Optical Properties of 4-Alkoxy-pyridine Butadiene Derivatives: Reversible Thermal Switching of Luminescence, *J Phys Chem C* (May 2, 2008), 112(22):8429-8437 (Abstract).

Liu et al., Fluorescent chemosensor for detection and quantitation of carbon dioxide gas, *J Am Chem Soc* (Oct. 13, 2010), 132(40):13951-13953 (Abstract).

Liu et al., Supramolecular Assembly of Perylene Bisimide with β-Cyclodextrin Grafts as a Solid-State Fluorescence Sensor for Vapor Detection, *Adv Funct Mater* (Jul. 24, 2009), 19(14):2230-2235.

Nie et al., Detection of TNT explosives with a new fluorescent conjugated polycarbazole polymer, *Chem Commun (Camb)* (Jan. 28, 2011), 47(4):1234-1236 (Abstract).

Schenning et al., Supramolecular electronics; nanowires from self-assembled π-conjugated systems, *Chem Commun (Camb)* (Jul. 14, 2005), 26:3245-3258 (Abstract).

Smith et al., Oxygen gas sensing by luminescence quenching in crystals of Cu(xantphos)(phen)+complexes, *J Am Chem Soc* (Oct. 13, 2010), 132(40):14079-14085 (Abstract).

Srinivasan et al., Reversible self-assembly of entrapped fluorescent gelators in polymerized styrene gel matrix: erasable thermal imaging via recreation of supramolecular architectures, *J Am Chem Soc* (Oct. 28, 2009), 131(42):15122-15123 (Abstract).

Stylianou et al., A guest-responsive fluorescent 3D microporous metal-organic framework derived from a long-lifetime pyrene core, *J Am Chem Soc* (Mar. 31, 2010), 132(12):4119-4130 (Abstract).

Takagai et al., "Turn-on" fluorescent polymeric microparticle sensors for the determination of ammonia and amines in the vapor state, *Analyst* (Jun. 2010), 135(6):1417-1425 (Abstract).

Takahashi et al., Dynamic vapochromic behaviors of organic crystals based on the open-close motions of S-shaped donor-acceptor folding units, *Chemistry* (Apr. 26, 2010), 16(16):4793-4802 (Abstract).

Wang et al., Fluorescent bio/chemosensors based on silole and tetraphenylethene luminogens with aggregation-induced emission feature, *J Mater Chem* (Oct. 19, 2009), 20:1858-1867 (Abstract).

Würthner, Plastic Transistors Reach Maturity for Mass Applications in Microelectronics, *Angew Chem Int Ed Engl.* (Mar. 16, 2001), 40(6):1037-1039.

Yoon et al., Multistimuli two-color luminescence switching via different slip-stacking of highly fluorescent molecular sheets, *J Am Chem Soc* (Oct. 6, 2010), 132(39):13675-13683 (Abstract).

Yu et al., Switching off FRET by analyte-induced decomposition of squaraine energy acceptor: A concept to transform 'turn off' chemodosimeter into ratiometric sensors, *Phys Chem Chem Phys* (Jul. 21, 2010), 12(27):7386-7391 (Abstract).

Zhang et al., Morphology control of fluorescent nanoaggregates by co-self-assembly of wedge- and dumbbell-shaped amphiphilic perylene bisimides, *J Am Chem Soc.* (Apr. 25, 2007), 129(16):4886-4887 (Abstract).

ACS, Chemistry for Life, Noteworthy Chemistry Articles, Nov. 21, 2011 http://portal.acs.org/portal/acs/corg/content?_nfpb=true&_pageLabel=PP_ARTICLEMAIN&node_id=840&content_id=CNBP_028716&use_sec=true&sec_url_var=region1&_uuid=7045f6a9-1b1e-494c-902b-3651a8278c14 (Printed from Internet Jan. 31, 2011).

An et al., Highly Sensitive Fluorescence Probes for Organic Vapors:On/off and Dual Color Fluorescence Switching, *Bulletin of the Korean Chemical Society* (2005), 26(10):1555-1559.

Carturan et al., Optical Properties of a Fluorinated Polyimide as Related to Ethanol and Water-Vapor-Sensing Capability, *IEEE Sensors Journal* (Dec. 2006), 6(6):1445-1453.

\* cited by examiner

CHROMOPHORES FOR THE DETECTION OF VOLATILE ORGANIC COMPOUNDS

CROSS-REFERENCE TO RELATED APPLICATION

This application claims benefit of and priority to International Provisional Application No. 3299/CHE/2011 entitled "Spectroscopic Probing Of The Dynamic Self-Assembly Of An Amphiphilic Naphthalene Diimide Exhibiting Reversible V Apochromism" filed Sep. 23, 2011, the disclosure of which is incorporated by reference in its entirety.

BACKGROUND

Volatile organic compounds (VOCs) are organic chemicals that have a high vapor pressure at ordinary, room-temperature conditions. The high vapor pressure results from a low boiling point, and this causes large numbers of molecules to evaporate or sublimate from the liquid or solid form of the compound and enter the surrounding air. VOCs are emitted as gases from various solids or liquids, and concentrations of many VOCs are consistently higher indoors (up to ten times higher) than outdoors. Some materials from which VOCs can be emitted include paints and lacquers, paint strippers, cleaning supplies, pesticides, building materials and furnishings, office equipment such as copiers and printers, correction fluids and carbonless copy paper, graphics and craft materials including glues and adhesives, permanent markers, and photographic solutions. Fuels are also made up of organic chemicals. All of these products can release organic compounds while in use and, to some degree, when stored.

Many VOCs are potentially dangerous to human health or cause harm to the environment. VOCs may have short-term and/or long-term adverse health effects. VOCs are typically not acutely toxic, but instead may have compounding long-term health effects. Some of the health effects of VOCs include eye, nose, and throat irritation, headaches, loss of coordination, nausea, liver, kidney, and central nervous system damage and cancer. Because the concentrations of VOCs are typically low and exposures usually occur over extended periods of time, symptoms may be slow to develop.

Accurate and sensitive detection of VOCs is critical because of the destructive nature of VOCs to human health and the environment, and because they are typically present in low concentrations. VOCs in the environment or certain atmospheres can be detected based on different principles and interactions between the organic compounds and the sensor components. Electronic devices may be capable of detecting concentrations of parts-per-million but are generally expensive. Other types of sensors may be less sensitive and/or have slow response times. In many cases, organic vapor sensors are designed to detect particular vapors, but providing a response to a variety of organic vapors may be more useful. Some exemplary uses of this nature may include indoor detection and leak or spill detection. Some organic vapor sensors function on the basis of fluorescence 'turn-off' upon exposure to organic vapors. These 'turn-off' sensors may exhibit a decrease in detection sensitivity due to background intensity. It is therefore desirable to provide a detector that can act as a fluorescence 'turn on' vapor sensor having high sensitivity and fast response for a broad range of VOCs.

SUMMARY

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In an embodiment, a sensor device for detecting a target substance includes a detection component of formula $R_1$—X—$R_2$ wherein X is an aromatic diimide, $R_1$ is an aliphatic alkyl or heteroalkyl, $R_1$ is bonded to X by an imide nitrogen, $R_2$ is an aliphatic alkyl or heteroalkyl, and $R_2$ is bonded to X by an imide nitrogen.

In an additional embodiment, a compound usable for detection of volatile organic compounds has a formula $R_1$—X—$R_2$, wherein X is an aromatic diimide, $R_1$ is an aliphatic alkyl or heteroalkyl, $R_1$ is bonded to X by an imide nitrogen, $R_2$ is an aliphatic alkyl or heteroalkyl, and $R_2$ is bonded to X by an imide nitrogen.

In a further embodiment, a method for detection of a target compound in a substance includes exposing an amphiphilic naphthalene diimide chromophore to the substance, wherein the amphiphilic naphthalene diimide chromophore changes from a first color to a second color in the presence of the target compound in the substance.

In an additional embodiment, a device for detecting the presence or absence of volatile organic compounds includes an amphiphilic aromatic diimide chromophore having a first color in the absence of volatile organic compounds and a second color in the presence of volatile organic compounds, the color of the amphiphilic aromatic diimide chromophore being reversibly interchangeable between the first color and the second color upon contact with volatile organic compounds and separation from contact with the volatile organic compounds.

DETAILED DESCRIPTION

Volatile organic compounds (VOCs) in the environment or certain atmospheres can be detected based on different principles and interactions between the organic compounds and the sensor components. Transition-metal assemblies for sensor applications are often based on the solvatochromic effect involving the ability of a chemical substance to change color due to a change in solvent polarity.

Alternative compounds exhibiting changes in fluorescence that result from molecular stacking interactions are less common. Vapochromic fluorescent organic materials formed by self-assembly have been determined to be usable for sensing VOCs. With such self-assembled materials exhibiting H-type and J-type stacking, changes in fluorescence can occur if organic vapors modulate the intermolecular interactions, and thus alter the molecular stacking of the self-assembly. Chromophores exhibiting aggregation induced enhanced emission (AIEE) phenomena have been found that provide 'turn off' vapor sensors.

Self-assembled chromophores having vapochromic 'turn on' fluorescence effects have been formed which exhibit the ability to be usable as sensors for targeted substances. Aromatic diimides of formula $R_1$—X—$R_2$, wherein X is the aromatic diimide, $R_1$ is an aliphatic alkyl or heteroalkyl, $R_1$ is bonded to X by an imide nitrogen, $R_2$ is an aliphatic alkyl or heteroalkyl, and $R_2$ is bonded to X by an imide nitrogen, have been formed which exhibit reversible changes in a physical attribute when in the presence or absence of various target substances. The substituents forming the diimide compounds can be selected so that the compounds exhibit a first manifestation of the physical attribute in the absence of the target substances, and a second manifestation of the physical attribute in the presence of the target substances, thereby enabling the diimides to be usable as detection devices for the target materials.

In one embodiment, $R_1$ or $R_2$ may be unsubstituted linear $C_{3-20}$ alkyls, substituted linear $C_{3-20}$ alkyls, unsubstituted branched $C_{3-20}$ alkyls, substituted branched $C_{3-20}$ alkyls, or combinations thereof. In an embodiment, $R_1$ or $R_2$ may be linear $C_{3-20}$ hydroxyls, linear $C_{3-20}$ halides, linear $C_{3-20}$ amides, linear $C_{3-20}$ carboxyls, linear $C_{3-20}$ sulfhydrils, linear $C_{3-20}$ phosphates, branched $C_{3-20}$ hydroxyls, branched $C_{3-20}$ halides, branched $C_{3-20}$ amides, branched $C_{3-20}$ carboxyls, branched $C_{3-20}$ sulfhydrils, branched $C_{3-20}$ phosphates or combinations thereof.

$R_1$ and $R_2$ may be the same substituent, or $R_1$ and $R_2$ may be different substituents, in which case, $R_1$ may be the aliphatic alkyl substituent and $R_2$ may be the heteroalkyl substituent. In a further embodiment, the aromatic diimide may be pyromellitic diimides, anthracene diimides, phenanthrene diimides, naphthalene diimides, perylene diimides, or combinations thereof.

In an alternative embodiment, $R_1$ or $R_2$ may be unsubstituted linear $C_{3-20}$ heteroalkyls, substituted linear $C_{3-20}$ heteroalkyls, unsubstituted branched $C_{3-20}$ heteroalkyls, substituted branched $C_{3-20}$ heteroalkyls, or combinations thereof having at least one carbon replaced by one of N, O, S, P, B, Si, or combinations thereof. Alternatively, $R_1$ or $R_2$ may be polyalkylene diols.

The aromatic diimide chromophores may exhibit vapochromic fluorescent effects upon being exposed to organic vapors or removed from the exposure to the organic vapors. Thus, a noticeable color change may occur which can indicate that an exposure to an organic vapor has occurred. And similarly, a reversible color change may occur which can indicate that the organic vapor is no longer present. Because of this change in fluorescence color, the diimide chromophores may be used in sensing devices for detection of organic vapors at concentrations less than about 100 ppm. The fluorescence may be enhanced by exposing the chromophores to a UV light source emitting light with a wavelength of about 300 nm to about 400 nm.

In an embodiment, the aromatic diimide chromophore may be applied to a support structure or substrate. The chromophore may be applied as a film or coating on the substrate. For example, the chromophore could be applied to a wall such as would be done by painting, or may be applied to a placard for being located in an area where VOCs may be present. The support structure may be in the form of a wearable badge, or an indicator card that could be placed or adhesively attached in an area that may possibly be subjected to an exposure of the target substance. Upon exposure to the target substance, the chromophore would exhibit a change in its physical appearance to indicate that an exposure to the substance has occurred. A reversible change in the physical appearance back to a pre-exposure state would be indicative that the target substance has been cleared from the area, or that the badge, etc. has been removed from the affected area.

In an embodiment, the targeted substances may be volatile organic compounds which may include, but are not limited to, the following compounds: acetaldehyde, ethylene oxide, di-(2-ethylhexyl)phthalate, formaldehyde, n-hexane, acrylonitrile, aniline, benzene, 2-methoxyethanol acetate, chloroethane, methyl ethyl ketone, chloroform, methyl isobutyl ketone, cumene, methyl methacrylate, cyclohexane, 4,4-methylene bis 2,4 aniline, 1,2-dibromoethane, phenylisocyanate, 1,2-dichloroethane, styrene, dichloromethane, 1,1,1,2-tetrachloroethane, tetrachloromethane, tetrachloroethylene, 2-ethoxyethanol, toluene, 2-ethoxyethanol acetate, tetrahydrofuran, 1,1,2-trichloroethane, ethyl acetate, trichloroethylene, ethyl butyl ketone, vinyl chloride monomer, ethylbenzene, xylenes, or combinations thereof.

The controlled self-assembly of fluorescent organic molecules in solution involves complex intermolecular interactions which significantly alter the molecular arrangements and hence the photo-physical properties. Therefore, to design and provide usable sensing devices, an understanding of the mechanism of self-assembly at the molecular level, as well as an understanding of the supramolecular organization of π-conjugated molecules can be beneficial. To better understand and characterize the molecular level of supramolecular systems in solution, spectroscopic functionality of the π-conjugated systems has been found to be usable to probe the self-assembly.

A spectroscopic analysis of the dynamic self-assembly process of an amphiphilic naphthalene diimide (NDI) derivative exhibiting reversible vapo- and thermochromism was conducted. An amphiphilic compound contains a relatively large organic cation or anion (X in the formula $R_1$—X—$R_2$) with long unbranched hydrocarbon chains (the $R_1$ and $R_2$ components). In one embodiment, $R_1$ or $R_2$ may be dodecyl. In an additional embodiment, $R_1$ or $R_2$ may be a polyethylene glycol, and the polyethylene glycol may be methoxy tetraethylene glycol.

In an embodiment, the aromatic diimide (X) is naphthalene diimide, and one example of an amphiphilic naphthalene diimide is represented by the structure:

wherein the $R_1$ component is dodecyl, and the $R_2$ component is methoxytetraethylene glycol. For the remainder of this disclosure, this compound as represented by the above structure will be referred to as NDI-Amph.

One method for preparing the NDI-Amph is by a statistical condensation reaction of 1,4,5,8-naphthalenetetracarboxylic dianhydride with methoxy tetraethylene glycol amine and dodecylamine, all three reactants in equivalent amounts (SI).

The corresponding bolaamphiphilic ($R_1$ and $R_2$ both being methoxy tetraethylene glycol) and di-dodecyl ($R_1$ and $R_2$ both being dodecyl) substituted derivatives were obtained as well.

Figure 1:
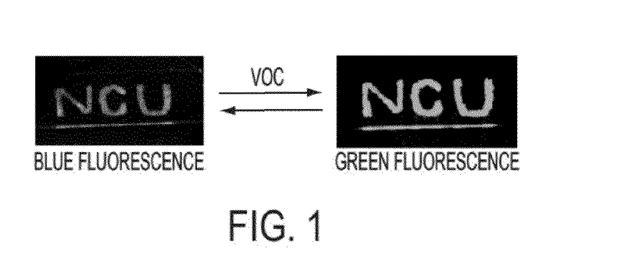
FIG. 1 depicts an illustrative example of visual changes in fluorescence of an aromatic diimide film upon exposure to volatile organic vapors according to an embodiment.

An observation of aggregation induced pre-associated excimer emission from NDI assemblies indicates that NDI assemblies may be suitable for fluorescent sensor applications as vapo-responsive NDI nanostructures. An unexpected vapochromic 'turn on' fluorescence effect was observed for films of the amphiphilic naphthalene diimide molecules (NDI-Amph) upon exposure to volatile organic vapors. As shown in FIG. 1, with illumination from a 365 nm UV light, NDI-Amph is able to exhibit a reversible change from blue fluorescence to green fluorescence upon exposure to VOCs and upon removal from the VOCs. Fluorescence changes are also observable when the film is heated to higher temperatures. Spectroscopic analysis indicates that this vapochromic behavior of NDI-Amph structures is due to a dynamic re-organization in molecular arrangement from J-type self-assembly to a fluorescent pre-associated H-type excimer state.

EXAMPLE 1

Synthesis and Characterization of an Aromatic Diimide Chromophore

An aromatic diimide chromophore, NDI-Amph was synthesized by the following steps:

1) 0.97 g (3.645 mmol) of 1,4,5,8-naphthalenetetracarboxylic dianhydride, 0.91 g (4.37 mmol) of methoxytetraethylene-glycolamine and 0.81 g (4.37 mmoles) of dodecylamine were mixed in a round bottom flask. (the molar ratio of the reactants is 1:1.2:1.2).
2) 25 ml of dimethylformamide (DMF) was added and the mixture was heated at 110° C. for 24 hours, in an inert gas $N_2$ atmosphere.
3) The solution was cooled and the DMF was evaporated under low pressure.
4) Residue was dissolved in chloroform ($CHCl_3$) and washed with water to remove any polar water soluble impurity.
5) The organic layer was dried over anhydrous sodium sulphate and solvent was evaporated to remove trace water content present in the chloroform.
6) The product was purified using silica gel column chromatography to isolate the NDI-Amph from the bolaamphiphilic and di-dodecyl substituted derivatives.

Figure 2A:
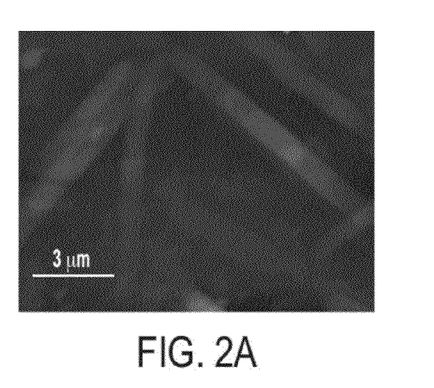
FIGS. 2a and 2b show microscopy images of an aromatic diimide in its J-state according to an embodiment.
Figure 2B:
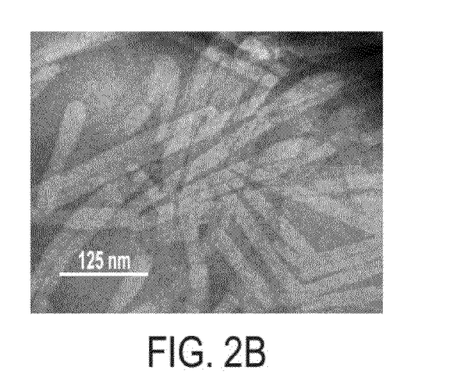

As shown in FIGS. 2a and 2b, detailed microscopic analysis of films obtained by drying dropcasted solutions of NDI-Amph showed bundles of nanotapes. FIG. 2a is from an atomic force microscope (AFM) and FIG. 2b from a transmission electron microscope (TEM). The films were obtained by drying a drop-casted ($1\times10^{-4}$ M) solution of NDI-Amph in 50% water in MeOH with 1% $CHCl_3$.

The NDI-Amph molecule was characterized by $^1H/^{13}C$ nuclear magnetic resonance spectroscopy (NMR) (AVANCE 400 (400 MHz)), electrospray ionization mass spectrometry (ESI-MS) and High Resolution Mass Spectrometry (HR/MS).

Substitutions at the imide positions make NDI-Amph soluble in most organic solvents like THF, $CHCl_3$ and toluene. Furthermore, the amphiphilic design may promote a surfactant-like self-assembly of otherwise weakly associating NDI aromatics in polar solvents like water through solvophobic and π-π interactions.

EXAMPLE 2

Spectroscopic Characterization of an Aromatic Diimide Chromophore

Figure 3A:
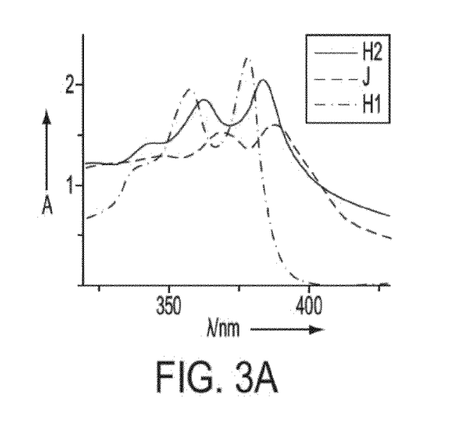
FIGS. 3a-3f show characteristic spectra and modeling of an aromatic diimide in various solvent compositions.
Figure 3B:
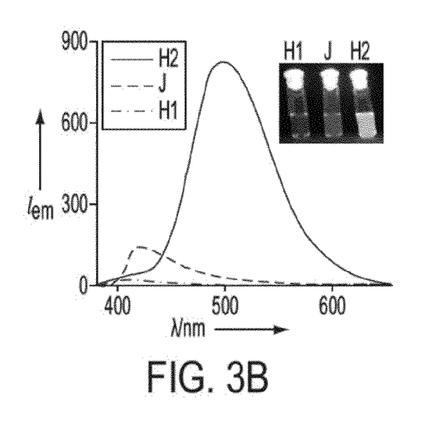

Since the optical properties of NDI-chromophores provide a means for probing molecular organization, a detailed spectroscopic study of NDI-Amph was conducted. As shown in FIGS. 3a and 3b, sharp absorption and emission bands of NDI-Amph in chloroform ($1 \times 10^{-4}$ M) with maxima at 380 nm and 408 nm, respectively, were visible. These bands are characteristic of the molecularly dissolved nature of NDI chromophores without any intermolecular interactions (M-state, FIG. 3c). All the solutions for the self-assembly studies were prepared by the injection of a solution of the molecularly dissolved NDI chromophores in $CHCl_3$ into MeOH/water solvent mixtures with varying compositions, since the NDI chromophores show intermolecular interactions in 100% MeOH solution. The various optical changes observed in these studies were consistent with a complex self-assembly process accompanying different polymorphic phases.

On increasing the percentage of water from 20% to 60% in MeOH (shown in FIGS. 3d-3f), the absorption bands undergo gradual bathochromic (9 nm, $\lambda_{abs}$=378 nm to 387 nm) and hypochromic shifts with the appearance of scattering (FIG. 3a), which could be due to the formation of J-aggregates. Careful observation of the corresponding emission spectra shows an increase in emission intensity (4 times) with a gradual red shift (14 nm, $\lambda_{em}$=407 nm to 421 nm) (FIG. 3e).

An unexpected enhancement of emission intensity on J-aggregation was observed since none of the known mechanism of aggregation induced enhanced emission (AIEE) were applicable. However, this unusual behavior was clarified by the optical spectroscopic studies of NDI-Amph in $CHCl_3$-MeOH solvent mixtures of various composition, which showed significant intermolecular interactions and a transition from monomeric M-state to a H-type self-assembled state at higher percentages of MeOH (c=$1 \times 10^{-4}$ M) (FIG. 3d). For example, the absorption spectra showed a gradual blue shift of the bands (2 nm, $\lambda_{abs}$=380 nm to 378 nm) with corresponding quenching (>3 times) in fluorescence ($\lambda_{em}$=408 nm), with increasing MeOH percentage in $CHCl_3$, which are characteristic signatures of an H-type self-assembly.

Since the H-type aggregates are non-fluorescent, the residual emission, even in 99% MeOH, suggests incomplete aggregation of chromophores at this concentration. Hence, a careful analysis of FIGS. 3d and 3e suggests that the enhanced emission of NDI-Amph on increasing percentage of water (0 to 60%) in MeOH with 1% $CHCl_3$ is due to the gradual shift from the non-fluorescent H-type self-assembly to the J-aggregates with red-shifted emission. A further increase in water (>60% water in MeOH) showed a gradual blue shift (5 nm, $\lambda_{abs}$=387 nm to 382 nm) in absorption with the appearance of remarkably intense green fluorescence with maxima at 497 nm (FIG. 3f). Although the blue shift in absorption spectra, on increasing water above 60% indicates the formation of a new type of H-aggregate, the broad unstructured emission band is a signature of excimer formation as shown in the case of analogous NDI derivatives.

Although H aggregates are known to undergo quenching of fluorescence due to rapid interband relaxation, it has also been reported that in co-facial H-dimer arrangements of n-conjugated chromophores, excitation can result in decreasing inter-chromophoric distance and that the resulting broad fluorescence band from a low energy state can be assigned to an excimer like state. To determine the nature of excimer formation, excitation spectra were recorded at monomer emission (430 nm) as well as excimer emission (500 nm) for the $1 \times 10^{-4}$ M solution of NDI-Amph in excimer state (70% water in MeOH with 1% $CHCl_3$). The excitation spectra collected at excimer emission is blue shifted ($A_{max}$=389 nm) compared to that collected at monomer emission ($A_{max}$=391 nm) reiterating the pre-associated H-type nature of the chromophore at this state. Further analysis of the self-assembly was not possible above 80% water in MeOH due to precipitation of the aggregates from solution.

Figure 3C:
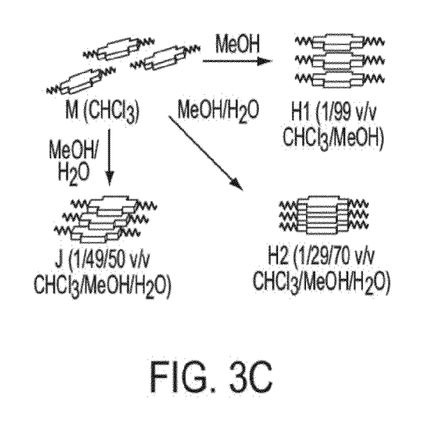
Figure 3D:
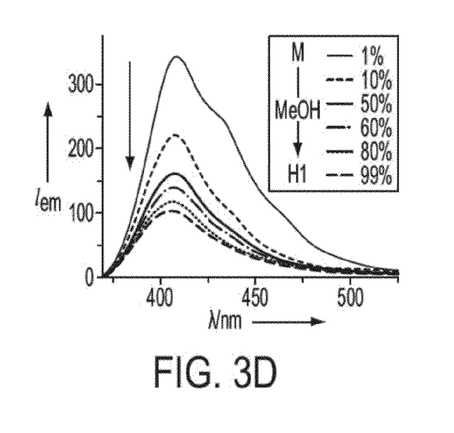
Figure 3E:
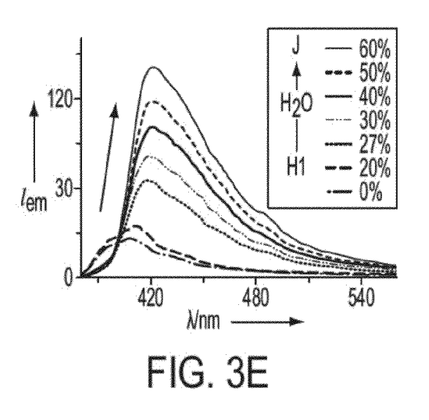
Figure 3F:
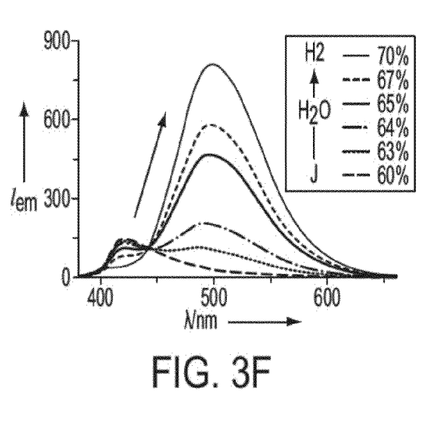

As a result of the detailed spectroscopic studies, the self-assembly of NDI-Amph appears to involve a complex energy landscape with various polymorphic phases which are sensitive to solvent composition (FIG. 3c). These states will be referred to as molecularly dissolved (M, $CHCl_3$ solution), H-assembly (H1, 1% $CHCl_3$ in MeOH), J-assembly (J, 50% water in MeOH with 1% $CHCl_3$) and H-type pre-associated excimer (H2, 70% water in MeOH with 1% $CHCl_3$).

EXAMPLE 3

Fluorescence Characterization of an Aromatic Diimide Chromophore

Figure 4:
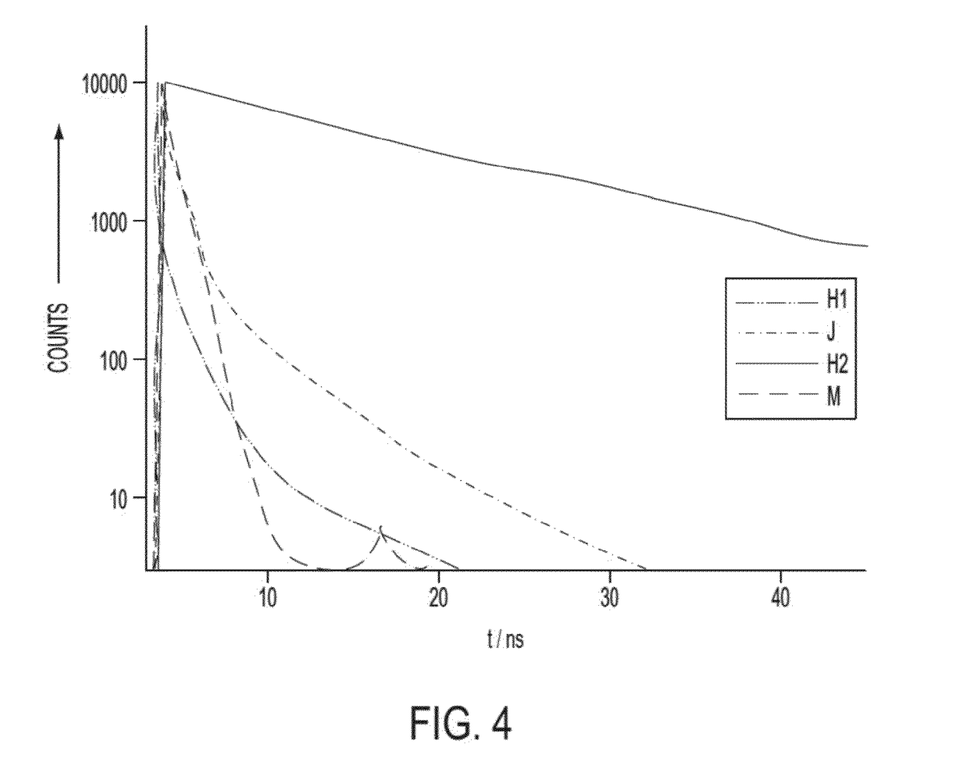
FIG. 4 illustrates fluorescence decay profiles of an aromatic diimide in its different polymorphic states according to an embodiment.

Time resolved fluorescence studies were carried out to characterize further and to understand the excited state dynamics of different polymorphic self-assembled states of NDI-Amph. FIG. 4 shows the fluorescence decay profile of NDI-Amph in various states with excitation at 385 nm. Emission at 440 nm for free molecules in chloroform (M) yielded a short lived mono-exponential decay (t=0.74 ns), whereas the H1 assembly decayed biexponentially ($\tau_1$=16 ps (77.26%), $\tau_2$=1.3 ns (22.74%)). J-state monitored at 440 nm exhibited a multi-exponential decay with life-times of 64 ps (19.37%), 0.91 ns (42.11%) and 3.94 ns (38.52%), characteristic of typical chromophores with intermolecular interactions. On the other hand, H2 excimer revealed a longer lived decay when monitored at 565 nm ($\tau$=13 ns) characteristic of the excimer emission. This long excited state lifetime was substantially high, which might not have formed within the life time of the excited state but rather arose from the pre-associated NDI-Amph in assemblies. Thus, the life-time studies reiterate the presence of three distinguished polymorphic states of self-assembly in agreement with steady state experiments.

EXAMPLE 4

Microscopic Characterization of an Aromatic Diimide Chromophore

Microscopic studies were also performed to obtain insight into the morphology of various polymorphic states of the NDI-Amph self-assembly. The J-self-assembled state in solution could be successfully transferred onto solid substrates (glass/copper grids) as evident from its retained characteristic optical properties as the solid substrate. A powder X-ray diffraction (PXRD) pattern of the resulting film showed peaks with higher order reflections indicating a three dimensional lamellar ordering of self-assembly. AFM, TEM and field emission scanning electron microscope (FESEM) studies of the J-state (FIG. 2a, 2b), showed nanotapes of 0.5-1 µm in width and several micrometers in length. Although the TEM analysis of the J-assembly could not reveal the bilayer packing in the tapes, much thinner ribbons with average width of 25 nm were able to be seen.

EXAMPLE 5

Vapochromic Characterization of an Aromatic Diimide Chromophore

Figure 5A:
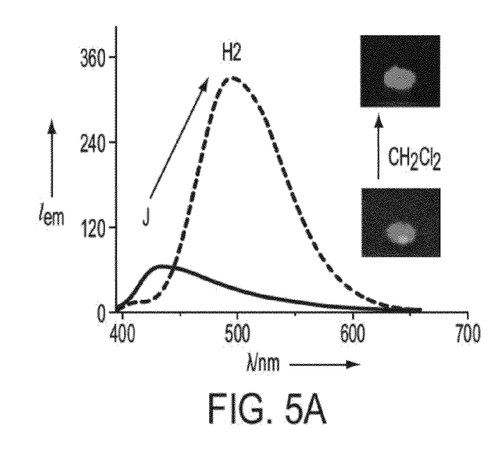
FIG. 5 shows emission spectra of NDI-Amph films in accordance with an embodiment.
Figure 5B:
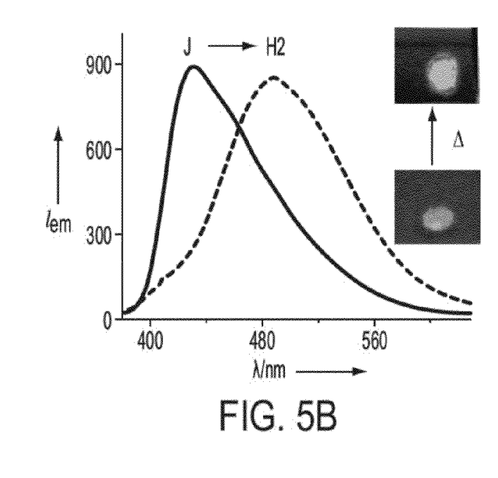
Figure 5C:
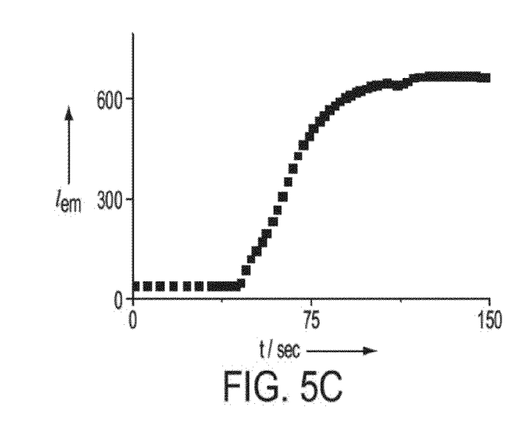
Figure 5D:
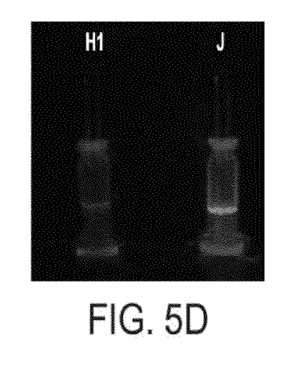

FIGS. 5a-5d show the vapochromic spectral changes accompanying the fluorescence switching process. FIG. 5a shows the emission spectra upon exposure to saturated vapors of $CH_2Cl_2$ and FIG. 5b upon being heated to high temperatures (normalized spectra). The inset of FIGS. 5a and 5b show the photographs of corresponding changes in the film under UV lamp with solvent vapors and temperature. FIG. 5c shows the time dependent evolution of the excimer emission ($\lambda_{em}$=500 nm) when the film is exposed to the solvent vapors, and FIG. 5d shows the H1 and J state solution of NDI-Amph upon exposure to vapors of $CHCl_3$ under UV illumination. Color changes were observed in a minute at the liquid-vapor interface which did not change further on prolonged exposure.

In the absence of vapors, the film shows an emission maximum at 434 nm similar to the J-type aggregates in solution, which gradually changes to the excimer emission with maxima at 497 nm and an increase in intensity, when exposed to vapors. Careful examination of the absorption and emission spectra suggest that the observed remarkable vapochromic behavior is due to the dynamic self-assembly transition from the J-aggregated state to the pre-associated H2-aggregate which results in the excimer emission as observed in the solution studies. Moreover, the 'turn-on' fluorescence of NDI-Amph was found to be very fast and reversible suggesting the dynamic nature of the self-assembled structures with vapors (FIG. 5c).

Similar changes in fluorescence were also observed when the film was subjected to high temperature. When the film in the J-state was heated to around 100° C., a very intense green fluorescence was observed (FIG. 5b). Films were exposed to a variety of volatile organic solvents like THF, dichloromethane, toluene, $CCl_4$, etc., and all the films showed excimer emission. On the other hand, on exposure to vapors of poor solvents for NDI chromophores, like MeOH, there was no such excimer formation, indicating that good solvents are required to induce molecular level reorganization in the J-assembly.

Preformed NDI-Amph J-assembly in solution also showed vapochromism as evident from the appearance of green emission at the solvent-vapor interface when exposed to saturated vapors of dichloromethane (FIG. 5d). Remarkably, the J-type molecular organization of the chromophores is found to be crucial for the vapochromism, as a solution of H1-assembly (99% MeOH in $CHCl_3$) did not respond to any volatile vapors. Further attempts to transfer the H1-assembly in solution to solid substrates, was not successful as it always resulted in the formation of J-aggregates on the surface which can be seen by the optical properties and microscopic analysis of the tape-like nanostructures.

This vapor responsive excimer emission from supramolecular aggregates provides a new design strategy for "turn on" VOC sensors, when compared to similar "turn-off" vapochromic sensors based on π-conjugated assembly.

EXAMPLE 6

Badge containing an Aromatic Diimide Chromophore for VOC Detection

An amphiphilic aromatic diimide, such as NDI-Amph, will be coated on a carrier substrate and formed into a badge which will have a clip assembly for a wearer to attach to an article of clothing. The badges will be provided to employees who have jobs with a risk of exposure (due to spillage, leakage, etc.) to several volatile organic compounds such as tetrahydrofuran, dichloromethane, chloroform, and toluene. The badges will be worn by the employees while performing their jobs.

As provided, the badges will exhibit their blue fluorescent color. Upon entering the work area, and throughout the workshift, the badges will remain blue unless a volatile organic compound is present. When the employee notes that the badge has turned green, they will be aware that a volatile organic compound is present, indicating precautionary steps need to be taken. These steps could involve evacuation of an area, ventilating an area, determining the cause of the exposure, etc.

When the employee and badges are removed from the affected area, and the badges are no longer exposed to the volatile organic compound, the badge color will return again to its original blue color for re-use If necessary, ultra-violet lighting will be provided for enhancing illumination of the badges.

EXAMPLE 7

Placards Containing an Aromatic Diimide Chromophore for VOC Detection

An amphiphilic aromatic diimide, such as NDI-Amph, will be coated on a carrier substrate and provided on placards which will be installed in various locations throughout a room in which there is a danger of exposure (due to spillage, leakage, etc.) to several volatile organic compounds such as tetrahydrofuran, dichloromethane, chloroform, and toluene. The placards will be illuminated with ultra-violet lighting to enhance the color of the chromophore.

As installed, the placards will exhibit a blue fluorescent color. Upon spillage or leakage of volatile organic compounds, the placards will change to a green color. When a placard is green, precautionary steps need to be taken. These steps could involve evacuation of the area, ventilating the area, determining the cause of the exposure, etc.

After the cause is found and the area ventilated to remove any residual vapors, the placards will turn blue again indicating that it is safe to return to the area.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A sensor device for detecting a target substance, the device comprising a detection component of formula 2. The device of claim 1, further comprising a support structure for retaining the detection component thereon, wherein the support structure comprises a surface and the detection component comprises a thin film on the surface of the support structure.

3. The device of claim 1, wherein the target substance comprises a volatile organic compound.

4. The device of claim 1, wherein the target substance comprises at least one of: acetaldehyde, ethylene oxide, di-(2-Ethylhexyl)phthalate, formaldehyde, n-hexane, acrylonitrile, aniline, benzene, 2-methoxyethanol acetate, chloroethane, methyl ethyl ketone, chloroform, methyl isobutyl ketone, cumene, methyl methacrylate, cyclohexane, 4,4-methylene bis 2,4 aniline, 1,2-dibromoethane, phenylisocyanate, 1,2-dichloroethane, styrene, dichloromethane, 1,1,1,2-tetrachloroethane, tetrachloromethane, tetrachloroethylene, 2-ethoxyethanol, toluene, 2-ethoxyethanol acetate, tetrahydrofuran, 1,1,2-trichloroethane, ethyl acetate, trichloroethylene, ethyl butyl ketone, vinyl chloride monomer, ethylbenzene, and xylenes.

5. The device of claim 1, wherein the detection component has an attribute having a first manifestation in the absence of the target substance and a second manifestation in the presence of the target substance.

6. The device of claim 5, wherein the attribute is reversibly interchangeable between the first manifestation and the second manifestation upon contact with and separation from the target substance.

7. The device of claim 6, wherein the attribute is color.

8. The device of claim 7, wherein the attribute is fluorescent color visible with ultra-violet illumination.

9. A device for detecting the presence or absence of volatile organic compounds, the device comprising
a chromophore of formula:

* * * * *